(12) United States Patent
Knüttel

(10) Patent No.: US 7,170,610 B2
(45) Date of Patent: Jan. 30, 2007

(54) LOW-COHERENCE INFEROMETRIC DEVICE FOR LIGHT-OPTICAL SCANNING OF AN OBJECT

(76) Inventor: Alexander Knüttel, Apfelstrasse 28, 69488 Birkenau (DE)

( * ) Notice: Subject to any disclaimer, the term of this patent is extended or adjusted under 35 U.S.C. 154(b) by 357 days.

(21) Appl. No.: 10/504,397

(22) PCT Filed: Feb. 1, 2003

(86) PCT No.: PCT/DE03/00288

§ 371 (c)(1),
(2), (4) Date: Aug. 11, 2004

(87) PCT Pub. No.: WO03/073041

PCT Pub. Date: Sep. 4, 2003

(65) Prior Publication Data

US 2005/0190371 A1    Sep. 1, 2005

(30) Foreign Application Priority Data

Feb. 21, 2002  (DE) .............................. 102 07 186

(51) Int. Cl.
*G01B 9/02* (2006.01)
*G01B 11/02* (2006.01)
*G01J 3/45* (2006.01)
(52) U.S. Cl. ...................... 356/456; 356/497; 356/511
(58) Field of Classification Search ................ 356/456, 356/479, 497, 489, 495, 511–515
See application file for complete search history.

(56) References Cited

U.S. PATENT DOCUMENTS 5,321,501 A    6/1994  Swanson et al.

(Continued)

FOREIGN PATENT DOCUMENTS

DE    43 09 056 A1    9/1994

(Continued)

OTHER PUBLICATIONS

Kwong, et al., "400-Hz Mechanical Scanning Optical Delay Line," Optics Letters; Apr. 1, 1993, 558-560; vol. 18, No. 7.

(Continued)

*Primary Examiner*—Gregory J. Toatley, Jr.
*Assistant Examiner*—Patrick Connolly
(74) *Attorney, Agent, or Firm*—Walter A. Hackler

(57) ABSTRACT

Low-coherence interferometric apparatus for light-optical scanning of an object (18) with a low-coherence interferometer (6) comprising a low-coherent light source (7), a reference reflector (21) and a detector (25), wherein light emitted by the light source (7) is split into two optical paths (11,12), a first fraction of the light being irradiated as measurement light (16) onto the object and a second fraction of the light being irradiated as reference light (22) upon the reference reflector (21), and wherein, after reflection on the object (18) or the reference reflector (21) respectively, the measurement light (16) and the reference light (22) are combined at a beam junction (10) in such a manner that an interference signal which contains information about the reflection intensity of the measurement light, relative to the respective scan position is generated.

Figure 1:
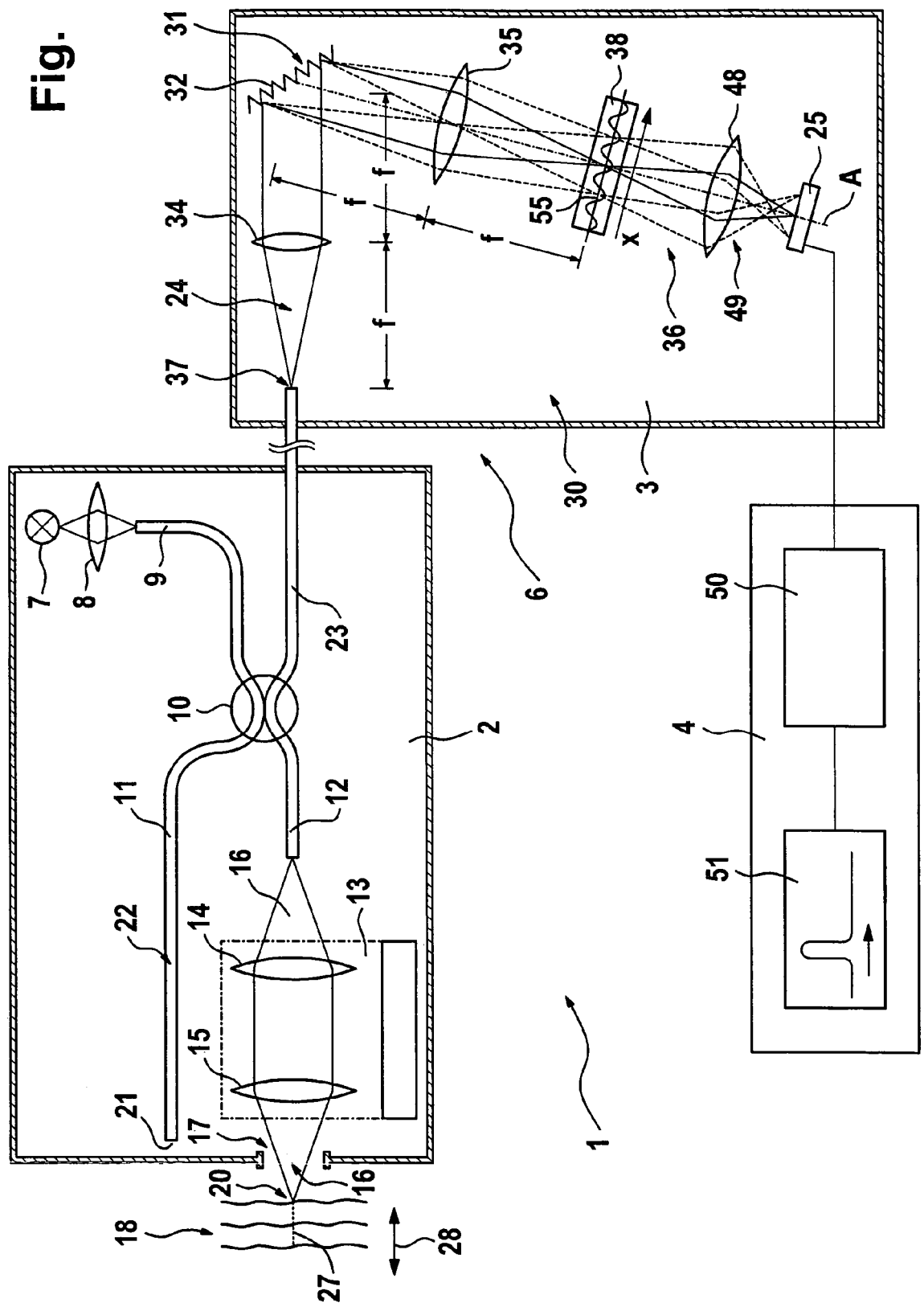

In order to enable a very fast scan, a variable wavelength selection device (30) is positioned in the light path of the detection light between the beam junction (10) and the detector (25). A wavelength-dependent selection of the detection light (24) is performed by this device in such a manner that the detector (25) selectively receives preferentially light with wavelengths which correspond to a predetermined sequence of wavenumbers k. For varying the scan position along the scan path (27) different sequences of wavenumbers k can be set.

11 Claims, 6 Drawing Sheets

U.S. PATENT DOCUMENTS

| | | | |
|---|---|---|---|
| 5,555,087 A * | 9/1996 | Miyagawa et al. | 356/497 |
| 5,565,986 A * | 10/1996 | Knuttel | 356/497 |
| 6,111,645 A | 8/2000 | Tearney et al. | |
| 6,144,456 A | 11/2000 | Chavanne et al. | |
| 6,775,007 B2 * | 8/2004 | Izatt et al. | 356/497 |
| 2004/0019283 A1 * | 1/2004 | Lambert et al. | 600/476 |
| 2004/0127778 A1 * | 7/2004 | Lambert et al. | 600/318 |
| 2006/0192975 A1 * | 8/2006 | Sato et al. | 356/497 |

FOREIGN PATENT DOCUMENTS

| | | |
|---|---|---|
| DE | 10033189 C1 | 9/2001 |
| DE | 19704602 A1 | 9/2001 |
| WO | WO 95/33971 | 12/1995 |
| WO | WO 97/27468 | 7/1997 |

OTHER PUBLICATIONS

J.M. Schmitt, "Compact In-Line Interferometer for Low-Coherence Reflectometry," Optics Letters, Feb. 15, 1995, 419-421; vol. 20, No. 4.

Tearney, et al., "High-Speed Phase- and Group-Delay Scanning With a Grating-Based Phase Control Delay Line," Optics Letters; Dec. 1, 1997, 1811-1813; vol. 22, No. 23.

* cited by examiner

LOW-COHERENCE INFEROMETRIC DEVICE FOR LIGHT-OPTICAL SCANNING OF AN OBJECT

The present invention refers to a low-coherence interferometric apparatus for light-optical scanning of an object by detecting the position of light-remitting sites which are located, at variable distances from the apparatus, along a scan path which extends in a scan direction (i.e. in the direction of the detection light beam; "z-direction"). Hereafter this is referred to as Low Coherence Distance Scan (LCDS).

Such apparatuses, and the corresponding methods are utilized for examining a variety of objects. They allow to determine, with a highest level of precision, the distance to one or a plurality of reflecting sites of an object or to provide a tomographical picture. Significant areas of use are the automatic measurement of object surfaces and analysis of the optical scattering behavior inside an object. The latter is especially significant in the medical field (tissue diagnostics).

In some applications it is sufficient to scan the object onedimensionally, i.e. only along a scan path which extends in the direction of the beam. Most cases of use, however, require to obtain, by means of an additional lateral scan, information about reflecting structures in a scan plane or (three-dimensionally) in a volume segment. This requires a two- or three-dimensional scan, which, in the simplest case, may be achieved by one- or two-dimensional lateral shifting of the interferometer. Such methods allow generation of a multidimensional tomographical picture and are commonly called OCT (Optical Coherence Tomography).

It is common to all LCDS methods that light of a low-coherent (spectrally broadband emitting) light source is split into two light paths, i.e. a measurement light path, which penetrates into the test specimen, and a reference light path. Before striking a detector, both partial light paths are combined in such a manner that interference occurs. To this end the apparatus contains an interferometer device, which, in addition to the low-coherent light source, usually contains a beam divider, a reference reflector and the detector. The light paths between these elements form interferometer arms. The light from the light source passes through a light source arm to the beam divider, where it is split. A first fraction of light is irradiated, as measurement light, onto the object in the scan direction, whilst a second portion of light, as reference light, reaches the reference reflector via a reflector arm. Both light fractions are reflected (the measurement light at light reflecting sites in the examined object, the reference light at the reference reflector) and travel back along the same light path (object arm, reference arm) to the beam divider. Here the light fractions are recombined and further transported as detection light via a detector arm to the detector.

During scanning, the longitudinal scan position is being varied in a fast sequence. Normally, this is achieved by changing the relationship of the path lengths of the reference light path and the measurement light path. Thereby the position along the scan path is varied, for which the conditions for interference of the measurement light and the reference light are met (namely that the optical path lengths of both light paths differ by no more than the coherence length of the light source). At each point of time the present scan position is the position on the scan path for which the optical length of the measurement light path is the same as the optical length of the reference light path (from the beam division to the beam junction; "Coherence condition").

Normally, the reference mirror is displaced in the direction of the reference beam, thereby reducing or increasing the length of the reference light path.

Further details about a plurality of known LCDS devices are described in corresponding literature sources, including the following publications:
1) WO 95/33971
2) J. M Schmitt "Compact in-line interferometer for low-coherence reflectometry", Optic Letters 1995, 419 through 421.
3) WO 97/27468.

The present invention refers especially to applications in which an extremely fast longitudinal scan is desired. An important example is the continuous examination of multi-layer foils (multi-foils) for production surveillance or quality control. The foil passes with high speed along a measurement head, and continuous control has to be applied to determine whether a certain desired foil thickness (for example 100 µm) is maintained within predetermined limits. Such cases of utilization require a very high scan speed. Assuming, for example, a surface spot diameter, to which the examination refers, of 8 µm and a travel speed of 10 m/sec, measurement data would have to be recorded approximately every 0.8 µsec. This corresponds to a minimum scan rate of 1.25 MHz. At 256 spots per longitudinal scan, this results in a repetition rate of 4.9 kHz. Such high repetition rates cannot be achieved by a mirror displacement.

Several proposals have been made to achieve a higher repetition rate with LCDS devices.

In the publication
4) K. F Wong et al: "400-Hz mechanical scanning optical delay line", Optics Letters 1993, 558–560, an optical retarding section is described, which may be integrated into the reference arm of an interferometer. The variation of the optical path length is achieved by a combination of an angular dispersion grating and a mirror which is pivotable within a very restricted angular range.

A similar device is also described in
5) U.S. Pat. No. 6,111,645 and
6) G. J. Tearney et al: High-speed phase- and group-delay scanning with a grating-based phase control delay line", Optics Letters 1997, 1811–1813, as part of a LCD device which is reported to be suitable for extremely fast scanning. In these publications, the basic principle used in citation 4) is generalized in the sense that a dispersion grating should be utilized in connection with a spectral phase shifter. Also non-mechanical possibilities for the realization of a spectral phase shifter, especially an acousto-optical modulator (AOM), are described.

A disadvantage of these proposals is the double passage of light through the retarding unit composed of the angular spectral grating and optical phase shifter which requires a very difficult alignment, since a precise reentrance into a single-mode light conducting fiber is required. Additionally, a high loss of intensity is caused by this light path.

Additional efforts for solutions proposed by the prior art are discussed in the initial sections of citations 5) and 6):

A modification of the optical path length may be achieved by piezoelectric fiber stretching. This, however, requires a relatively large-sized unit and does not allow a sufficiently high repetition rate. In addition, the energy consumption is high.

The longitudinally moveable mirror in the reference channel may be replaced by a pivoting glass cube (see also U.S. Pat. No. 6,144,456). This causes, however, a non-linear change of the optical path length and a dispersion which depends on the optical path length. Again, the achievable repetition rates do not satisfy high requirements.

Based on this situation the technical problem addressed by the present invention is to provide an interferometric apparatus which allows, with tolerable expenditure, an extremely high repetition rate of longitudinal scanning.

This problem is solved by a low-coherence interferometric apparatus for light-optical scanning of an object, by detecting the position of light-remitting sites which are located along a scan path running in a scan direction, with a low-coherence interferometer comprising a low-coherent light source, a reference reflector and a detector, wherein light emitted from the light source is split by a beam divider into two optical paths and a first fraction of the light is irradiated as measurement light onto the object and reflected at a light-remitting site located at a variable scan position on the scan path, and a second fraction of the light is irradiated as reference light onto the reference reflector where it is reflected, the adjustable scan position is varied along the scan path to perform a scan, and the measurement light and the reference light are combined at a beam junction in such a manner that the resulting detection light, upon striking the detector, generates an interference signal which contains information about the reflection intensity of the measurement light relative to the respective scan position, characterized in that a variable wavelength selection device is positioned in the light path of the detection light between the beam junction and the detector, by which a wavelength-dependent selection of the detection light is performed in such a manner that the detector selectively receives preferably light with wavelengths which correspond to a predetermined sequence of wavenumbers k, and different sequences of wavenumbers k can be set for varying the scan position along the scan path.

Contrary to the above explained earlier efforts to achieve extremely fast longitudinal scans, the scanning unit for setting the scan position is integrated in the light path of the detection light downstream from the joining of the reference light and the measurement light. According to the invention the variation of the longitudinal scan position is not based on a change of the relationship of the length of measurement- and reference light paths, but on a selection of a sequence of wavelengths of the interfering detection light. This selection is varied by means of the wavelength selecting device in such a manner that the sequence of wavenumbers ("k-profile of the wavelength selecting device) corresponding to the selected wavelengths coincides with that k-profile of the interferometer which corresponds to the respective scan position. This will hereafter be explained in detail, based on the figures.

The physical phenomenon utilized in the invention has been known for a long time as so-called "Müller stripes". Occasionally, it was also used in the context of interferometric methods. DE 4309056 describes the possibility to determine the distance of light scattering sites, i.e. their intensity distribution in the direction of the detection beam, by spectrally decomposing the light by means of a spectral device, the spectrum being detected with a location-sensitive light detection device, for example a row of photodiode cells. According to the document this arrangement allows to determine by Fourier transformation the intensity distribution of the detected spectrum. This method is inadequate for fast longitudinal scans, since by far too much time is required for data interpretation of the photodiodes and processing by means of a Fourier transformation. Additionally, the detector signal is quite weak in view of the required good local resolution. Therefore the S/N (signal/noise) ratio is bad.

Several important advantages are achieved by the invention:

A complete longitudinal scan may be accomplished with a very high repetition rate (10–100 kHz). For many applications, especially for the continuous inspection of moving objects, it is important that an even higher scanning frequency per scanning site (1–10 MHz) is possible.

The measurement head of the device can be miniaturized very well, since the scanning unit is disposed in the detection light path, which can be connected with the remaining portions of the interferometer, which may be integrated into a compact measurement head, by means of light conducting fibers.

Evaluation is not dependent upon phase-sensitive information in the detection light path and is, therefore, quite robust. Also the risk of signal distortions caused by misalignment is relatively low.

The light intensity recorded by the detector is high (especially as compared with DE 4309056), since no location-selective detection is required.

In case that the optical dispersion in the measurement light path is different from the dispersion in the reference light path, this results with prior devices in a lack of signal precision. In the context of the present invention, such dispersion differences may be offset by correspondingly adjusting the k-profile of the wavelength selecting device.

Figure 2:
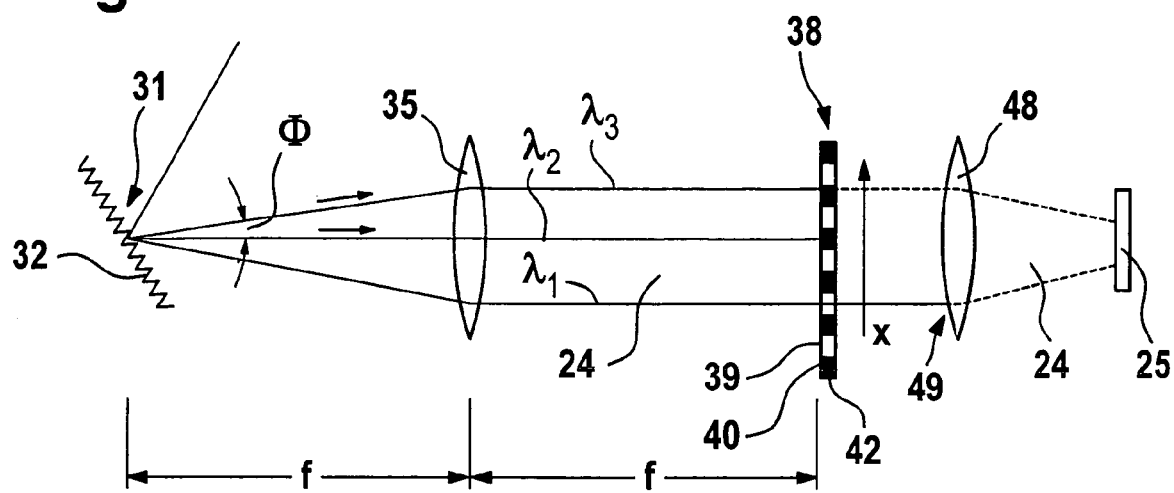
Figure 3:
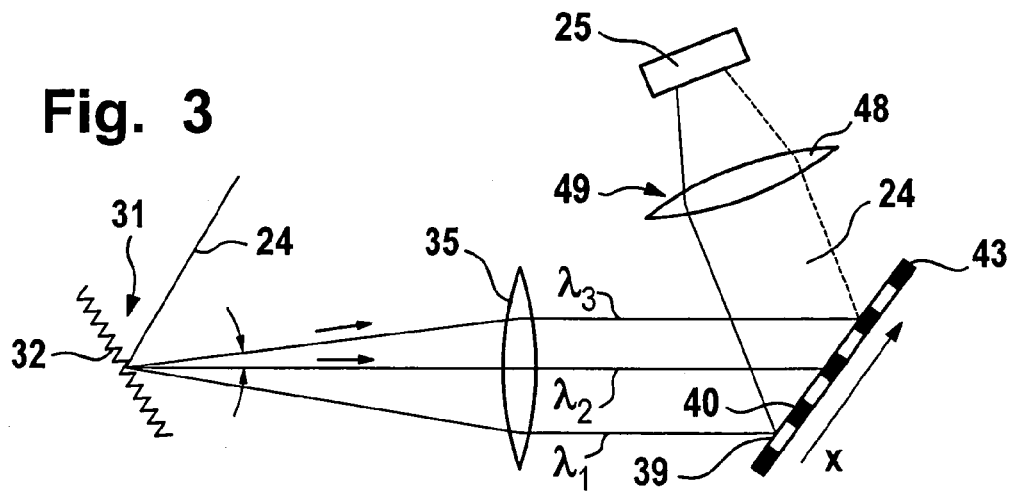
Figure 4:
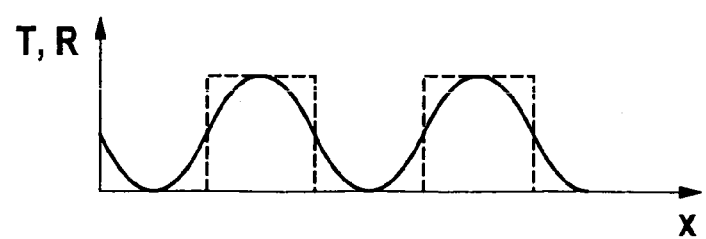
Figure 5:
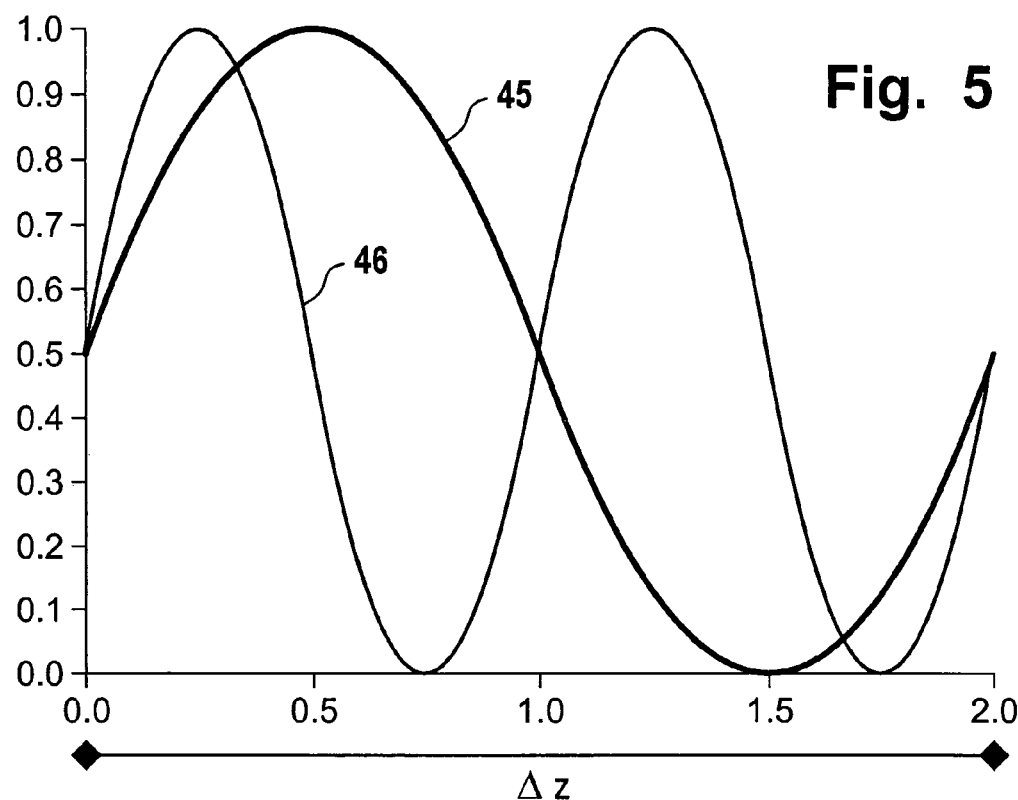
Figure 6:
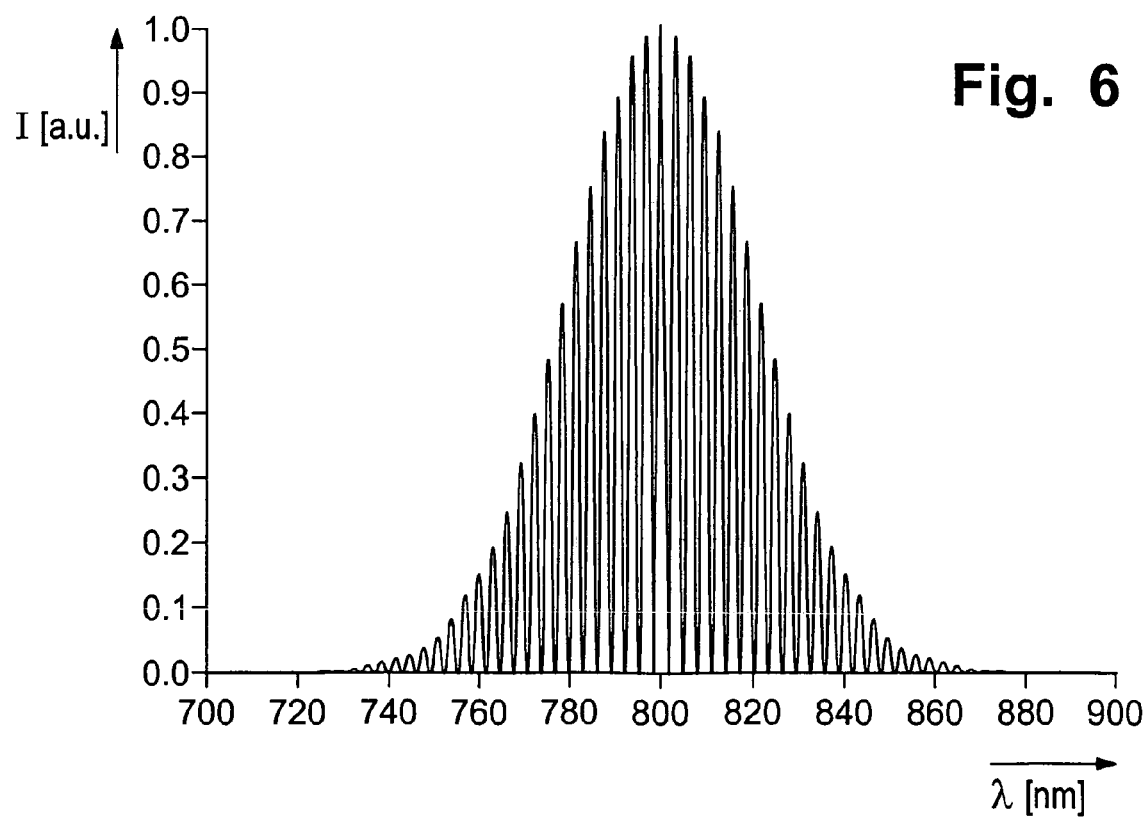
Figure 7:
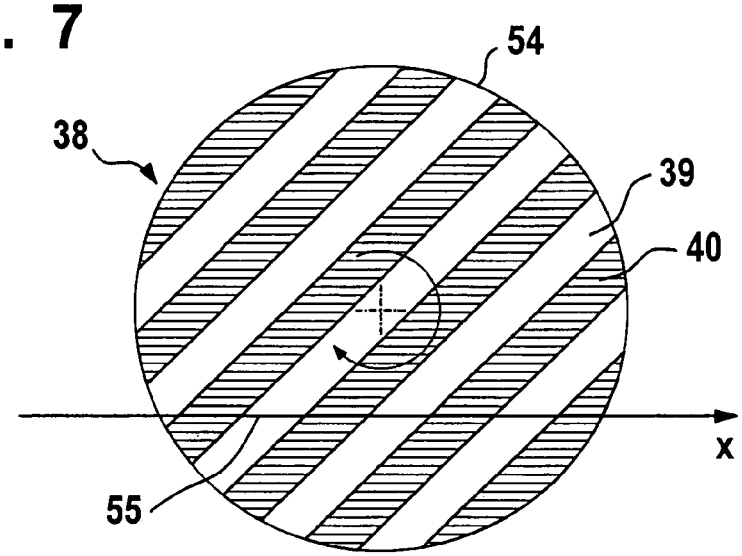
Figure 8:
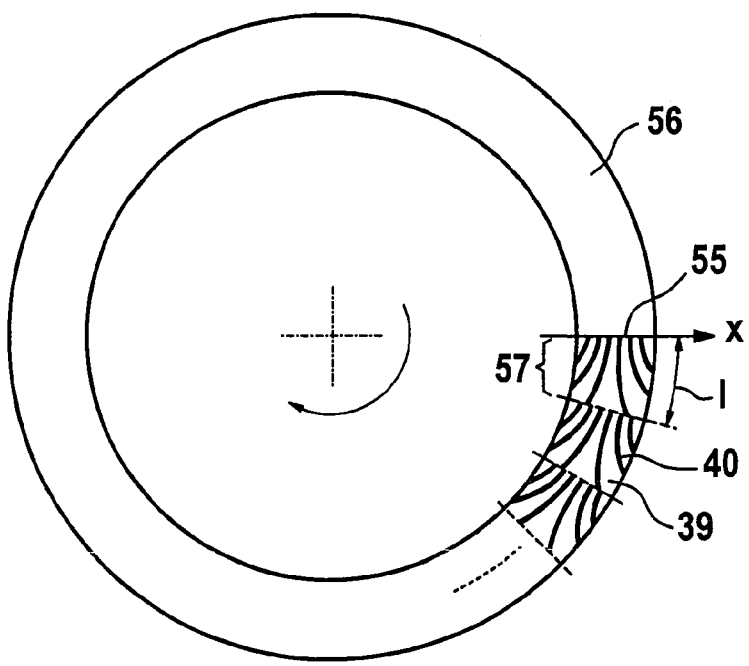
Figure 8A:
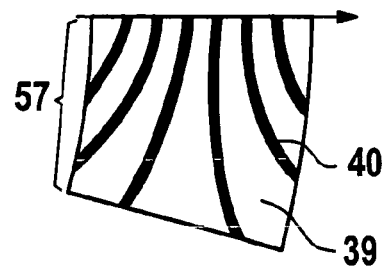
Figure 9:
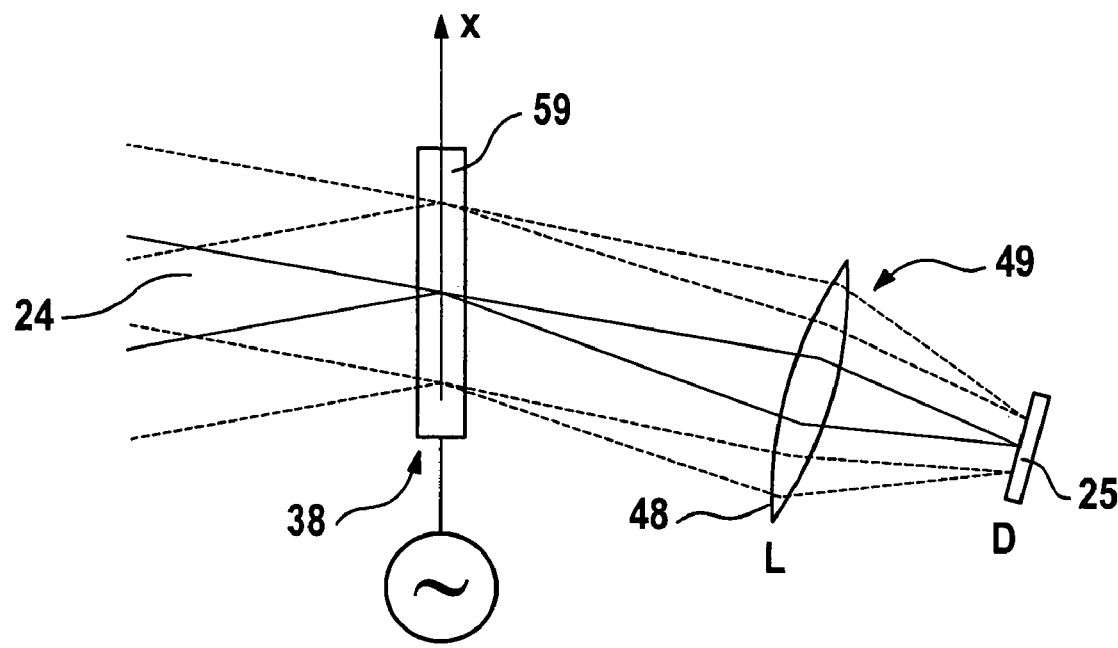
Figure 10:
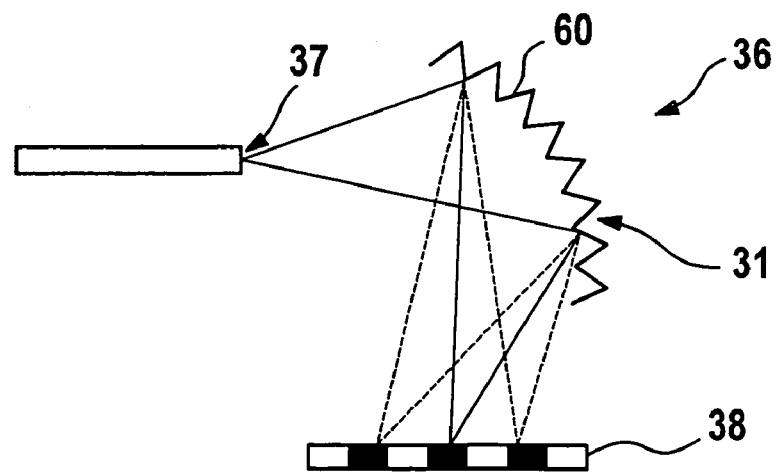
Figure 11:
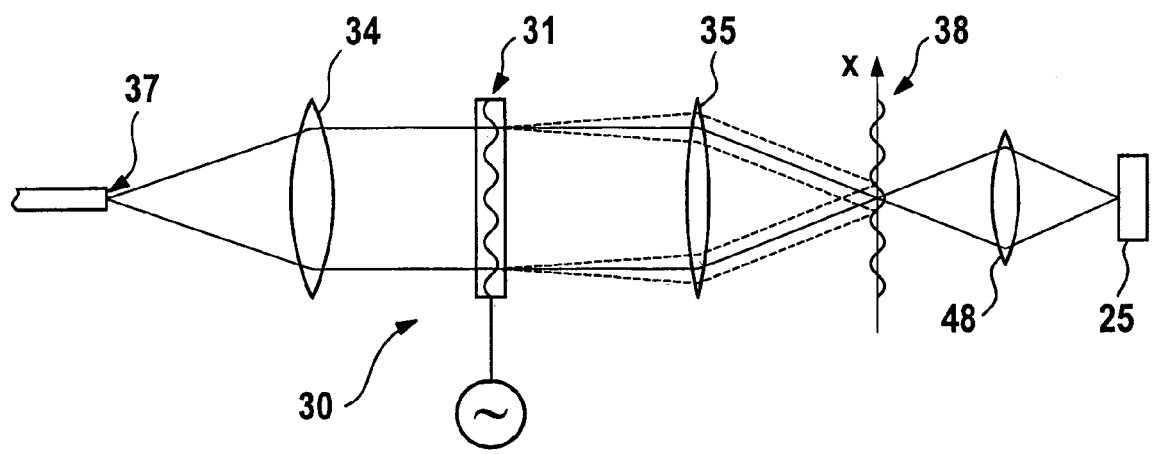
Figure 12:
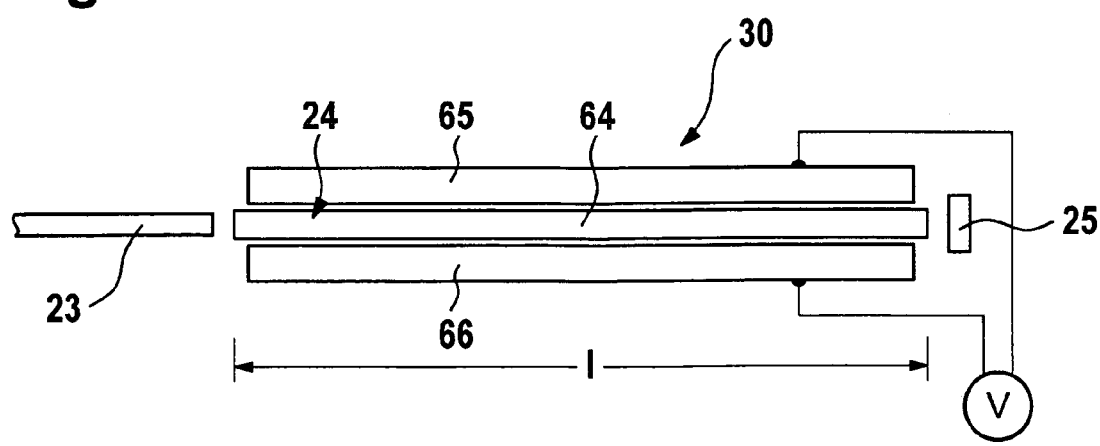

Hereafter the invention will be explained in more detail, based on exemplary embodiments shown in the figures. The features shown and described may be used separately or in combination to create preferred embodiments of the invention. In the figures:

FIG. 1 shows a schematic representation of a LCDS apparatus according to the invention, FIG. 2 shows a schematic representation of a part of a first embodiment of a variable wavelength selection device, FIG. 3 shows a schematic representation of a part of a second embodiment of a wavelength selection device, FIG. 4 shows a diagram to explain the analog and digital selection by means of a spatial light selection device, FIG. 5 shows a graphical representation of the superposition of two different wavelengths, FIG. 6 shows a graphical representation of the k-profile of an interferometer when the measurement light is reflected by a light-remitting site located at a defined scan position, FIG. 7 shows a schematic representation of a first embodiment of a mechanically variable spatial light selection device, FIG. 8 shows a schematic representation of a second embodiment of a mechanically variable spatial light selection device, FIG. 8a shows an enlarged cutout of FIG. 8, FIG. 9 shows a schematic representation of a part of a third embodiment of a wavelength selection device, FIG. 10 shows a schematic representation of a part of a fourth embodiment of a wavelength selection device, FIG. 11 shows a schematic representation or a part or a fifth embodiment of a wavelength selection device, FIG. 12 shows a schematic representation of part of a sixth embodiment of a wavelength selection device.

The LCDS apparatus 1 shown in FIG. 1 consists of a measurement head 2, a scanning unit 3 and an electronic unit 4. The representation is not to scale and is strongly schematic. Constructive details which are not essential for the function of the invention are not shown.

The measurement head 2 and the scanning unit 3 contain the optical components of a low-coherence interferometer 6. The light of a light source 7 is coupled via a lens 8 into a single-mode light conducting fiber which forms the light source arm 9 of the interferometer 6. The primary light transported in light source arm 9 is equally divided by means of an optical coupler 10, acting as a beam divider, as measurement light 16 into a sample arm 12 and, as reference light 22 into a reference arm 11, in which arms the light transport also takes place inside light conducting fibers. In the sample arm 12, the measurement light 16 is coupled out by means of an objective 13, composed of lenses 14 and 15. Lens 15 refocuses the measurement light 16 radiated through aperture 17 towards a test specimen 18.

Both in sample arm 12 and in reference arm 11 a reflection takes place, namely at a light-remitting site 20 of the measurement object 18 and at a reference reflector 21, respectively. The reflected measurement light 16 and the reflected reference light 22 are recombined in optical coupler 10 and are transported as detection light 24 in a detection arm 23 towards detector 25.

Up to this point, the construction of the interferometer 6 is essentially conventional and therefore needs not be explained in more detail. Instead of the shown interferometer device, another known configuration can also be used. Especially, instead of the optical fiber version using an optical fiber coupler 10, a free beam arrangement with a free beam splitter can be used. In principle, it is also possible to use separate optical elements as beam divider for light separation on the one hand and as beam uniting elements on the other hand. Preferably, however, the same optical element 10 is used for beam division and junction, as shown.

A specific feature of the interferometer device contained in the measurement head 2 is that neither the reference arm 11 nor the sample arm 12 contain means, by which the lengths of both arms (generally expressed, the lengths of the measurement light path and reference light path) are changed relative to each other in order to vary the longitudinal scan position along a scan section 27, shown in dotted lines in FIG. 1, in the scan direction symbolized by arrow 28. Rather the variation of the scan position, which is required to accomplish the longitudinal scan, is produced by means of the scanning unit 3 integrated into the light path of the detection light 24, between the junction of the light (by means of the optical coupler 10) and the detector 25.

Scanning unit 3 contains a variable wavelength selection device, generally designated 30, whose essential components may be seen more clearly in FIGS. 2 and 3, in two different embodiments. In the preferred case shown, it comprises a spectral separation device 31, by which the detection light 24 is spatially separated, dependent on its wavelength λ. In the case shown, the spectral separation device 31 is formed by a reflecting spectral grating 32. However, also other optical elements (transmission gratings, prisms), commonly used in spectral devices may be chosen. Spectrally separated light reflected from spectral grating 32 is focused onto a spatial light selection device 38, by means of an optical imaging system 36 which is composed of two objectives 34 and 35. The first objective 34 collimates light emitted from entrance pupil 37 of the wavelength selection device 30 onto the spectral separation device 31, while the second objective 35 focuses light emitted from the spectral separation device 31 onto the light selection device 38.

The spatial light selection device 38 has light passage areas 39 and light blocking areas 40, alternately disposed along a line, which preferably is straight and extends in a spatial direction which is designated x in the figures. In any case, the line of the alternating light passage and blocking areas 39,40 must extend transversally to the optical axis A of detection light 24, such that light which, dependent on its wavelength, is spatially separated along the line by the spectral separation device 31 strikes the alternating light passage and blocking areas in such a manner that it is transported towards the detector 25 with alternating intensity, corresponding to the wavelength.

This may be achieved both with a transmission device, shown in FIG. 2 and with a reflection device, shown in FIG. 3. Detection light 24 passes through the light passage areas 39 with less attenuation, as compared to the blocking areas 40. For example, in FIGS. 2 and 3, light with wavelength $\lambda_1$ striking the central section of a light passage area 39 reaches detector 25 practically without attenuation, whereas light with wavelength $\lambda_2$ centrally striking a blocking area is blocked nearly completely. Light striking with wavelengths $\lambda_3$ between a light passage area and a blocking area, is partially attenuated. Based on FIG. 3, it becomes apparent that the expressions "light passage area" and "light blocking area" should not be understood, in a limiting manner, in the sense of a transmission device where light passes through an optical element. On the contrary, the desired alternating degree of attenuation may also be caused by a reflecting optical element.

FIG. 4 shows that in both cases of light selection, i.e. the transmitting spatial light selecting device 42 according to FIG. 2, as well as the reflecting spatial light selection device 43 shown in FIG. 3, the transmission T and reflection R, respectively, of the element varies, dependent on position x, preferably in analog (especially sinusoidal) manner. Digital selection, shown in figure in dotted lines is, however, also possible. It is decisive that light selected according to the defined k-profile of the wavelength selection device 30 is preferentially transported to the detector 25. Preferably, the difference between the minimum light attenuation of wavelengths corresponding to the k-profile and the maximum light attenuation of the "blocked" wavelengths ("selection contrast") should be as large as possible.

According to the embodiments of the invention shown in FIGS. 1 through 3, the variable light wavelength selection, in accordance with the k-profile of the wavelength selection device 30, is achieved with a constant angular dispersion of the wavelength-dependent light separation, in combination with a variation of the distance of the alternating light passage and blocking areas 39,40 of the spatial light selection device 38. Alternatively, it is also possible (and explained hereafter, based on FIG. 11) to use a spectral separation device 31 with variable angular dispersion in combination with a constant spatial light selection device 38. In principle, it is also possible that both these elements are variable.

For example an electrically operated LCD mask may be used as transmitting variable spatial light selection device 38 (FIGS. 1 and 2). In this case, the minimum distance of adjacent transmission areas is given by twice the pixel distance of the mask. Larger distances may be adjusted stepwise as multiples of this distance. An approximately analog transmission variation may be achieved if the pixel distance is much smaller than the shortest desired distance between the transmission areas.

In this respect a reflection device of the type shown in FIG. 3, where a DMD (Digital Mirror Device) can be used as variable light selection device, is especially advantageous. Such micromirror arrays are produced with extremely small pixel distances, especially for projection systems.

Hereafter, the principle used according to the invention will be explained, based on FIGS. 5 and 6.

FIG. 5 shows, along a path $\Delta z$, the superposition of two wave trains 45 and 46, oscillating in phase at the origin (zero point). At the end of path $\Delta z$ the wave trains are again in phase, thus constructively interfering with each other. It can be directly derived from the figure that two wave trains interfere constructively under the conditions shown, when their wavelength is an integer fraction of $\Delta z$, i.e. when the condition $\lambda = \Delta z/n$ applies.

For the purpose of simplification, only two wave trains were considered here. In reality, an interference of many adjacent wave trains takes place. By considering the correlation between wavenumber k and wavelength $\lambda$ ($k=2\pi/\lambda$) the general rule may be derived that along a path $\Delta z$ those wave trains interfere constructively, whose wavenumbers differ by $$\Delta k = 2\pi/\Delta z. \qquad (1)$$

Such interference also takes places in the detection arm of an interferometer. The origin zero point from which path length $\Delta z$ is measured, is defined by the point of the measurement light path for which the optical path lengths of the measurement light path and the reference light path are identical. Hereafter, it will be designated "point of coincidence of optical lengths". In the context of the invention, the coincidence point is significant in two ways:

a) On the one hand, it marks the point for which the coherence condition explained further above is met. In the common LCDS devices, this represents the basis for longitudinal scanning.

b) At the same time, it marks the position at which the measurement and reference light are in phase for all wavelengths (provided there are no differences of optical dispersion). The coincidence point is, therefore, the zero point of the longitudinal scan according to the invention. The actual scan position is located at a distance $\Delta z$ from the coincidence point.

FIG. 6 shows an interference spectrum resulting from such a superposition (wavelength-depended intensity normalized to the maximum value) in case of a light source with a central wavelength $\lambda_o = 800$ nm and a spectral band width $\Delta\lambda_{FWHM} = 50$ nm for an interference path length $\Delta z = 100$ µm.

Such a spectrum may be experimentally observed by placing a reflector in the measurement light beam of a LCDS device according to FIG. 1 at a distance $\Delta z$ from the coincidence point of the interferometer and by analyzing, at the position of the spatial light selection device 38, the intensity variation in x-direction along line 55, i.e. the dependence of intensity upon the wavelength (by means of a locally sensitive or displaceable detector). The k-profile of the interferometer in the k-space corresponds, for the chosen value of $\Delta z$, to this spectrum in the $\lambda$-space.

From the above equation (1) a direct relation of the distance of the maxima of the k-profile and $\Delta z$ can be derived mathematically. Consequently, in k-space the points of maximum interference of the k-profile of the interferometer are equidistant, as long as it is not required to consider differences of optical dispersion between the measurement light path and the reference light path. Setting of a longitudinal scan position at a distance $\Delta z$ from the coincidence point is therefore possible by setting the variable wavelength selection device 30 to an equidistant sequence of wavenumbers k, whose distances $\Delta k$ are calculated in accordance with equation 1. Since the correlation between $\lambda$ and k is not linear (rather reciprocal) the corresponding spectrum in $\lambda$-space is not strictly equidistant. When considering a relatively narrow band spectrum, as shown in FIG. 6 the sequence of the selected $\lambda$-values is, however, approximately constant, too.

As repeatedly mentioned, the preceding considerations are based on the assumption that no optical dispersion has to be taken into account, i.e. the dependence of the refractive index of the wavelength in the measurement light path is the same as in the reference light path. In commonly used LCDS devices, the spatial resolution of the scan signal is negatively influenced by dispersion differences. Therefore considerable efforts are usually made to achieve, by an adequate choice of the light conducting means, as much similarity of the optical dispersion of both light paths as possible. In the context of the present invention it is, however, possible to offset in a simple manner the dispersion differences between the light path of the measurement light 16 and the light path of the reference light 22, by choosing the sequence of the wavenumbers k which are selected by the longitudinal wave selection device 30, deviating from an equidistant sequence, in such a manner that the difference in dispersion is offset. In other words, the k-profile of the wavelength selection device is adapted to the k-profile of the interferometer, which is not equidistant, considering the dispersion. Experimentally, this may take place in a relatively simple manner by positioning a reflector in a plurality of different scan positions on the scan path 27 and, for example as above described, measuring the resulting spectrum in the detection light path of the interferometer. According to this procedure a k-profile of the interferometer is obtained for each scan position within the $\Delta z$ range. The same k-profiles are also selected by the wavelength selection device 30 and varied to accomplish a longitudinal scan.

After passage of the wavelength selection device 30, selected light 24 strikes the photosensitive surface of a detector 25. The detector 25 is not locally selective, i.e. it transforms the entire light intensity which it receives into an electrical signal which is transferred to the electronic unit 4, where it is evaluated. According to the preferred embodiment shown in FIGS. 1 to 3, a condenser lens 48 is arranged in front of the detector 25, acting as light collecting element 49. It is thus possible to capture, with a comparative small detector surface, the entire light which passes through the wavelength selection device 30.

Inside electronic unit 4, the intensity of light captured by detector 25, is recorded by an evaluation unit 50, dependent on the setting of the k-profile of the wavelength selection unit 30. To each k-profile, the corresponding value of the scan position $\Delta z$ is allocated. The intensity of the measurement signal, after deducting a base line (i.e. the difference of the intensity from the base line signal), corresponds to the intensity of the reflection at the respectively selected scan position.

Although scanning is not based on a modification of the relation of the optical wavelengths of the measurement light path (measured up to the coincidence point) and of the reference light path, this does not mean that the position of the reference reflector 21 in the reference light path must be constructively fixed. On the contrary, for the purpose of the alignment of the device, it can be advantageous to make this position adjustable. During the scanning procedure, however, the length of the reference light path remains constant.

FIGS. 7 and 8 show two different embodiments of a light selection device 38 which may be mechanically varied. A common feature of both is that on a pivotable disc 54 and 56, respectively, light passage and blocking areas 39,40 are provided in the form of stripes which extend in such a manner that their stripe distance, measured along a line 55 running across the disk surface, varies during rotation of the disk. The light passage and blocking areas may be produced in any desired shape, for example by photo-lithographic processing of a metal-coated glass plate.

In the case of the disk 54 shown in FIG. 7 the light passage areas 39,40 are straight and parallel. A line 55 which is effective regarding the wavelength selection (i.e. the line, upon which the spectrum of the spectral separation device is projected) runs in such a manner that the effective distance of areas 39,40 varies when the disk 54 rotates.

In the embodiment shown in FIGS. 8 and 8a, the light passage and blocking areas 39,40 converge at a border stripe 56 over sections of length l towards each other in such a manner that their distance, relative to line 55, upon which the spectrum is projected, decreases in each segment 57 during rotation. During the passage of a segment 57, a complete scan takes place, so that a very high scan speed is achieved. For example, with a rate of 100 rotations per second and 100 segments 57 (with replicated structures), a repetition rate of 10 kHz may be achieved. Since the curvature of the line structure of areas 39,49 may be chosen freely, it is possible to adapt the light selection with respect to dispersion differences of the measurement- and reference lights paths.

In connection with FIGS. 2 and 3, the possibility was already described to utilize for the spatial light selection device 38 an optical element (LCD, DMD) which allows selective setting of transmission or reflection in different partial sections of its surface by electronic means. Another example of this general principle is shown in FIG. 9. In this case the detection light 24 originating from the spectral separation device 31 is focused on the surface of an AOM (Acousto-Optical Modulator). Inside the AOM, continuous sound waves are generated. The resulting vibrations in the crystal (which consists, for example, of TeO$_2$) result in a spatial light selection under an angle which corresponds to the first order diffraction. Detector 25 and condenser lens 48 are arranged at this diffraction angle relative to the optical axis of light striking AOM 59. Contrary to the earlier described embodiments, the light passage and blocking areas 39,40 of the spatial light selection device 38 formed by AOM 59 are not stationary on its surface, but move continuously in x-direction. The function of the invention is, however, not negatively affected by this fact.

FIG. 10 shows that the optical imaging function, required in scanning unit 30, not necessarily has to be provided by additional construction elements. For example an arcuate spectral grating 60 may be utilized as a spectral separation device 31. It provides not only the spectral separation, but also the required collimation of the light coming from the entrance pupil 37 onto the spatial light selection device 38.

As already stated, FIG. 11 shows an alternative embodiment of the variable wavelength selection device 30. Here a spectral separation device 31 with variable spreading is used in combination with a constant spatial light selection device 38. In this case the detection light 24 coming from entrance pupil 37 and collimated by objective 34 is spectrally separated by an AOBD (Acousto-Optic Beam Deflector). The AOBD forms a variable spectral grating having a grating distance which depends on the applied electrical frequency. By means of the second objective 35, the resulting spectral components are focused upon a constant spatial light selection device 38.

FIG. 12 shows a variable wavelength selection device 30 which is basically different from the earlier described embodiments inasmuch as it is not based upon the combination of a spectral separation device with a spatial selection device. Here, detection light 24 coming from the detection light guide 23 is coupled into a light guide 64 with partially reflecting terminal faces having a refractive index which depends on the electrical field intensity. Photoconductor 64 is surrounded by two electrodes 65, 66 to which a variable voltage V can be applied in order to vary the electrical field strength inside the photoconductor 64. Based on the Fabry-Perot Effect, the alteration of the refractive index in photoconductor 64 caused by the alteration of the electrical field strength results in a variation of the optical path which, in turn, causes a light wave selection due to interference.

The invention claimed is:

1. Low-coherence interferometric apparatus for light-optical scanning of an object (18), by detecting the position of light-remitting sites (20) which are located along a scan path (27) running in a scan direction (28),
with a low-coherence interferometer (6) comprising a low-coherent light source (7), a reference reflector (21) and a detector (25), wherein
light emitted from the light source (7) is split by a beam divider (10) into two optical paths (11, 12), and a first fraction of the light is irradiated as measurement light (16) onto the object and reflected at a light-remitting site (20) located at a variable scan position on the scan path (27), and a second fraction of the light is irradiated as reference light (22) onto the reference reflector (21) where it is reflected,
the adjustable scan position is varied along the scan path (27) to perform a scan, and
the measurement light (16) and the reference light (22) are combined at a beam junction (10) in such a manner that the resulting detection light (24), upon striking the detector, generates an interference signal which contains information about the reflection intensity of the measurement light relative to the respective scan position,
characterized in that a variable wavelength selection device (30) is positioned in the light path of the detection light between the beam junction (10) and the detector (25), by which a wavelength-dependent separation of the detection light (24) is performed in such a manner that the detector (25) selectively receives preferably light with wavelengths which correspond to a predetermined sequence of wavenumbers k, and different sequences of wavenumbers k can be set for varying the scan position along the scan path (27).

2. Apparatus according to claim 1, characterized in that, in the spectral range of the light source (7), the optical dispersion in the light paths of the measurement light (16) and the reference light (22) is essentially the same and the sequence of wavenumbers k is equidistant.

3. Apparatus according to claim 1, characterized in that, in the spectral range of the light source (7), the optical dispersion in the light path of the measurement light (16) differs from the optical dispersion in the light path of the reference light (22) and the sequence of wavenumbers k deviates in such a manner from the equidistant sequence that the dispersion difference is compensated.

4. Apparatus according to claim 1 characterized in that the variable wavelength selection device (30) comprises
a spectral separation device (31) by which the detection light (24) is spatially separated, dependent on the wavelength of the detection light (24),
a spatial light selection device (38) having, alternating along a line, light passage areas (39) with lower light attenuation and light blocking areas (40) with higher light attenuation, the detection light (24) passing with less attenuation through the light passage areas (39) than through the blocking areas (40), and an optical imaging system (34, 35) by which light irradiated from the spectral separation device (31), is focused upon the spatial light selection device (38), wherein the spreading of the wavelength-dependent separation of the detection light (24) by the spectral separation device (31) and the distance of the alternating passage and blocking areas (39, 40) of the light selection device (38) are variable relative to each other for setting the sequence of wavenumbers k.

5. Apparatus according to claim 4, characterized in that the angular dispersion of the wavelength-dependent light separation by the spectral separation device (31) is constant and the distance of the alternating light passage and blocking areas (39, 40) of the light selection device (38) is variable.

6. Apparatus according to claim 5, characterized in that the spectral separation device (31) comprises an optical grating (32).

7. Apparatus, according to claim 4 characterized in that at least on optical element 60 of the optical imaging system (36) is simultaneously a component of the spectral separation device (31).

8. Apparatus, according to claim 4 characterized in that the spatial light selection device comprises a reflective optical element (43), upon which the detection light (24) is irradiated and which selectively provides different reflection in the light passage areas (39) and in the blocking areas (49).

9. Apparatus according to claim 1 characterized in that the light selection device (38) comprises a rotatable disk (54, 56) with light passage and blocking areas (39, 40) in the form of stripes, running in such a manner that a distance thereof, measured along a line (55) extending over the disk surface, changes during rotation of the disc (54, 55).

10. Apparatus according to claim 1 characterized in that the spatial light selection device (38) comprises an optical element (42, 43, 59) having a reflection or transmission which can be selectively adjusted in different partial areas thereof by electronic means.

11. Apparatus according to claim 1 characterized in that a light-collecting optical element (49) is positioned in the light path of the detection light (24) between the light selection device (38) and the detector (25), in order to concentrate the detection light (24) on the detector (25).

* * * * *